United States Patent [19]
Lindemann et al.

[11] Patent Number: 5,958,738
[45] Date of Patent: Sep. 28, 1999

[54] PROCEDURE FOR SUBTRACTIVE HYBRIDIZATION AND DIFFERENCE ANALYSIS

[75] Inventors: Garrett W. Lindemann; Paula A. Schueler, both of Benicia, Calif.

[73] Assignee: Roche Diagnostics Corporation, Indianapolis, Ind.

[21] Appl. No.: 08/823,111

[22] Filed: Mar. 24, 1997

[51] Int. Cl.⁶ .................................................. C12P 19/34
[52] U.S. Cl. ........................................................... 435/91.2
[58] Field of Search ............................................. 435/91.2

[56] References Cited

U.S. PATENT DOCUMENTS

| | | | |
|---|---|---|---|
| 4,683,202 | 7/1987 | Mullis .................................... | 435/91.2 |
| 5,418,149 | 5/1995 | Gelfand et al. ......................... | 435/91.2 |
| 5,436,142 | 7/1995 | Wigler et al. ........................... | 435/91.2 |
| 5,501,964 | 3/1996 | Wigler et al. ........................... | 435/91.2 |
| 5,518,900 | 5/1996 | Nikiforov et al. ...................... | 435/91.1 |
| 5,525,471 | 6/1996 | Zeng ......................................... | 435/6 |

FOREIGN PATENT DOCUMENTS

| | | |
|---|---|---|
| 2093567 | 8/1994 | Canada . |
| WO 8912695 | 12/1989 | WIPO . |
| WO 93/05149 | 3/1993 | WIPO . |
| WO 9640998 | 12/1996 | WIPO . |

OTHER PUBLICATIONS

Baldocchi et al., "Recovery of probes linked to the jcpk locus on mouse chromosome 10 by the use of an improved representational difference analysis technique" *Genomics* (1996) 33:193–198.

Bolli et al., "Watson–Crick base–pairing properties of bicyclo–DNA" *Nucl. Acids Res.* (1996) 24:4660–4667.

Cherny et al., "DNA unwinding upon strand–displacement binding of a thymine–substituted polyamide to double–stranded DNA" *Proc. Natl. Acad. Sci. USA* (1993) 90:1667–1690.

Demers et al., "Enhanced PCR amplification of VNTR locus D1S80 using peptide nucleic acid (PNA)" Nucl. Acids Res. (1995) 23:3050–3055.

Demidov et al., "Kinetics and mechanism of polyamide ("peptide") nucleic acid binding to duplex DNA" *Proc. Natl. Acad. Sci. USA* (1995) 92:2637–2641.

Don et al., "'Touchdown' PCR to circumvent spurious priming during gene amplification" *Nucl. Acid Res.* (1991) 19:4008.

Gurr et al., "PCR–directed cDNA libraries" in *PCR—A Practical Approach*, 1991, IRL Press, McPherson et al., eds., pp. 147–170.

Hedrick et al., "Isolation of cDNA clones encoding T cell–specific membrane–associated proteins" *Nature* (1984) 308:149–153.

Higuchi et al., "Production of single–stranded DNA templates by exonuclease digestion following the polymerase chain reaction" *Nucl. Acids Res.* (1989) 17:5865.

Hou et al., "A simplified genomic subtractive procedure for isolating deleted sequences" *Nucl. Acids Res.* (1996) 24:2196–2197.

Hubank et al., "Identifying differences in mRNA expression by representational difference analysis of cDNA" *Nucl. Acids Res.* (1994) 22:5640–5648.

Innis et al., "Optimization of PCRs" in *PCR Protocols: A Guide to Methods and Applications* (1990), Academic Press, Innis et al., eds., pp. 3–12.

Kerr et al., "Gene 6 exonuclease of bacteriophage T7" *J. Biol. Chem.* (1972) 247:311–318.

Kunkel et al., "Specific cloning of DNA fragments absent from the DNA of a male patient with an X chromosome deletion" *Proc. Natl. Acad. Sci. USA* (1985) 82:4778–4782.

Lamar et al., "Y–encoded, species–specific DNA in mice: Evidence that the Y chromosome exists in two polymorphic forms in inbred strains" *Cell* (1984) 37:171–177.

Lebeau et al., "PCR driven DNA—DNA competitive hybridization: a new method for sensitive differential cloning" *Nucl. Acids Res.* (1991) 19:4778.

Lisitsyn et al., "Cloning the differences between two complex genomes" *Science* (1993) 259:946–951.

Lisitsyn et al., "Direct isolation of polymorphic markers linked to a trait by genetically directed representational difference analysis" *Nature Genetics* (1994) 6:57–63.

Lisitsyn et al., "Representational difference analysis in detection of genetic lesions in cancer" *Meth. Enzymol.* (1995) 254:291–304.

Mathieu–Daudé et al., "DNA rehybridization during PCR: the '$C_o t$ effect' and its consequences" *Nucl. Acids. Res.* (1996) 24:2080–2086.

Nielsen et al., "Sequence–selective recognition of DNA by strand displacement with a thymine–substituted polyamide" *Science* (1991) 254:1497–1500.

Nikiforov et al., "The use of phosphorothioate primers and exonuclease hydrolysis for the preparation of single–stranded PCR products and their detection by solid–phase hybridization" *PCR Methods and Applications* (1994) 3:285–291.

(List continued on next page.)

*Primary Examiner*—Terry McKelvey
*Attorney, Agent, or Firm*—Morrison & Foerster, LLP

[57] ABSTRACT

Improved methods for obtaining polynucleotides comprising sequences which differ between two populations of DNA or cDNA are provided. Improvements include reduction in the number of amplification cycles, use of a nuclease digestion step prior to amplification, a novel oligonucleotide adapter for the practice of the improved method, and novel methods for selective amplification of the desired unique fragments and selective degradation of fragments containing sequences common to both populations. Fragments of a sample population are amplified using a primer that endows the amplification products with resistance to nuclease degradation. Fragments of a control population are amplified using a primer that targets the amplification products for preferential degradation. Multiple cycles of hybridization, nuclease treatment and amplification are utilized to provide enrichment of fragments unique to the sample population. Such unique fragments may represent new or amplified sequences in the sample population, sequences that are differently arranged in the sample population compared to the control population, and sequences that are differentially expressed in a cDNA population. A variation of the technique also allows the isolation of fragments representing deletions in the sample population.

21 Claims, 1 Drawing Sheet

OTHER PUBLICATIONS

Nussbaum et al., "Isolation of anonymous DNA sequences from within a submicroscopic X chromosomal deletion in a patient with choroideremia, deafness, and mental retardation" *Proc. Natl. Acad. Sci. USA* (1987) 84:6521–6525.

Patanjali et al., "Construction of a uniform–abundance (normalized) cDNA library" *Proc. Natl. Acad. Sci. USA* (1991) 88:1943–1947.

Peffer et al., "Strand–invasion of duplex DNA by peptide nucleic acid oligomers" *Proc. Natl. Acad. Sci. USA* (1993) 90:10648–10652.

Pope et al., "Can PCR be used to normalise a cDNA library?" *Biochem. Soc. Trans.* (1995) 23:383S.

Saiki et al., "Primer–directed enzymatic amplification of DNA with a thermostable DNA polymerase" *Science* (1988) 239:487–491.

Sargent et al., "Differential gene expression in the gastrula of *Xenopus laevis*" *Science* (1983) 222:135–139.

Straus et al., "Genomic subtraction for cloning DNA corresponding to deletion mutations" *Proc. Natl. Acad. Sci. USA* (1990) 87:1889–1893.

Wang et al., "A gene expression screen" *Proc. Natl. Acad. Sci. USA* (1991) 88:11505–11509.

Wetmur et al., "Nucleic acid hybridization and unconventional bases" in *PCR Strategies* (1995), Academic Press, Innis et al., eds., pp. 69–83.

Wetmur, "DNA probes: Applications of the principles of nucleic acid hybridization" *Critical Reviews in Biochem. and Molecular Biol.* (1991) 26:227–259.

Wieland et al., "A method for difference cloning: Gene amplification following subtractive hybridization" *Proc. Natl. Acad. Sci. USA* (1990) 87:2720–2724.

Wittwer et al., "Rapid cycle DNA amplification" *The Polymerase Chain Reaction* (1994) Burkhauser, Boston, K.B. Mullis et al., eds., Chapter 15, pp. 174–181.

Zeng et al., Differential cDNA cloning by enzymatic degrading subtraction (EDS) *Nucl. Acids. Res.* (1994) 22:4381–4385.

Zhu et al., "Enrichment of DNA fragments for deleted sequences in human genome with nuclease digestion and PCT amplification" *Nucl. Acids Res.* (1994) 22:2428–2429.

Applied Biosystems Model 380 DNA Synthesizer User's Manual, Chapter 2, "Chemistry for Automoated DNA Synthesis" (Unnumbered Pages and No Author Given).

Luk'yanov et al., "Highly Efficient Subtractive Hybridization of cDNA," Journal of Bioorganic Chemistry, vol. 20(6):386–388 (1994).

Sambrook et al., *Molecular Cloning*, Cold Spring Harbour Press, US pp. 5.84–5.86 (1990).

Yang et al., "Cloning Differentially Expressed Genes by Linker Capture Subtraction," Analytical Biochemistry, vol. 237:109–114 (1996).

Flow Diagram for Improved Subtractive Hybridization and Difference Analysis

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (xi) SEQUENCE DESCRIPTION: SEQ ID NO:1:

CGATAGTCAC TCTACCACTC AGCCTACGCA CGAGACGATG TACTC      45

(2) INFORMATION FOR SEQ ID NO:2:

(i) SEQUENCE CHARACTERISTICS:
       (A) LENGTH: 13 base pairs
       (B) TYPE: nucleic acid
       (C) STRANDEDNESS: single
       (D) TOPOLOGY: linear (xi) SEQUENCE DESCRIPTION: SEQ ID NO:2:

GATCGAGTAC ATC      13

(2) INFORMATION FOR SEQ ID NO:3:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:3:

CGATAGTCAC TCTACCACTC AG      22

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

TAGTCACTCT ACCACTCAGC CTAC        24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

TACCACTCAG CCTACGCACG AGAC        24

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

CAGCCTACGC ACGAGACGAT GTACTC        26

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:7:

CAGCCTACGC ACGAGACGAT GTACTC        26

PROCEDURE FOR SUBTRACTIVE HYBRIDIZATION AND DIFFERENCE ANALYSIS

CROSS-REFERENCE TO RELATED APPLICATIONS

Not Applicable

STATEMENT OF RIGHTS TO INVENTIONS MADE UNDER FEDERALLY SPONSORED RESEARCH

Not Applicable

TECHNICAL FIELD

The invention is in the field of genetic analysis. The invention relates to methods for isolation of polynucleotides comprising nucleic acid sequences which are differentially expressed, differentially present, or differentially arranged in two or more different cells, cell populations or cell types, utilizing techniques of subtractive hybridization and selective amplification.

BACKGROUND OF THE INVENTION

The ability to detect differences between two populations of nucleic acid sequences is important to characterizing the molecular basis of various pathological states, for example neoplasia, infectious and degenerative diseases, viral infections and hereditary predisposition to disease. Increasingly, the technique of subtractive hybridization is being used to identify polynucleotides comprising sequences that are present in a first population of nucleic acid sequences but absent, present in a different concentration, or arranged differently in a second population.

Sargent and Dawid, Science 222:135–139 (1983) used subtractive hybridization to isolate cDNAs representing mRNA molecules preferentially expressed at the gastrula stage of development of the frog embryo. Gastrula cDNA was hybridized to RNA from unfertilized eggs and the cDNA that failed to hybridize was cloned. These cloned sequences represented mRNAs that were differentially expressed in the frog gastrula. Similarly, Hedrick et al., *Nature* (London) 308:149–153 (1984) cloned a T-cell receptor molecule by hybridizing cDNA from antigen-specific T-cells with RNA from B-cells and collecting the non-hybridized cDNA. Despite these early successes, it soon became evident that this method is limited in practice to detection of differentially-expressed mRNA representing 0.01% or more of the total mRNA population. Furthermore, in cases where the method is practical, selection of the differentially expressed cDNA (as single-stranded material) is achieved by hydroxyapatite chromatography, which is cumbersome and results in losses of valuable material. Finally, this technique did not provide a method to detect differences in genome organization, such as deletion, gene amplification, or rearrangement.

Adaptations of the subtractive hybridization technique have been developed which allow the identification and isolation of polynucleotides representing sequence differences between different genomes. Lamar and Palmer, *Cell* 37:171–177 (1984) used a selective cloning approach to isolate Y chromosome-specific sequences in the mouse. Hybridizations were conducted using restriction enzyme-digested male DNA as tracer and sonicated female DNA as driver. Of the duplexes obtained after annealing, only those with both strands derived from male DNA contain sequences unique to the Y chromosome and possess a restriction enzyme recognition site at each end. Such duplexes were cloned preferentially into a vector containing compatible restriction enzyme-generated ends.

Kunkel et al., *Proc. Natl. Acad. Sci USA* 82:4778–4782 (1985) and Nussbaum et al., *Proc. Natl. Acad Sci USA* 84:6521–6525 (1987) described the isolation of fragments containing sequences deleted from the human X chromosome by hybridization of restriction enzyme-digested DNA from cells that were polysomic for the X chromosome with an excess of sheared DNA from cells harboring one or more X chromosome deletions, using conditions in which the rate of reassociation was enhanced. Selective cloning using a vector with compatible restriction enzyme-generated ends was used for the isolation of sequences absent in the X chromosome deletions.

Strauss and Ausubel, *Proc. Natl. Acad. Sci. USA* 87:1889–1893 (1990) described a technique for isolating a polynucleotide comprising DNA that is absent in a yeast deletion mutant. In this method, denatured wild-type DNA is allowed to anneal with biotin-labeled DNA from the deletion mutant, and biotin-containing duplexes (which contain sequences common to the mutant and wild-type) are removed from solution by binding to avidin-coated beads. The process is repeated for several cycles, with addition of fresh biotinylated wild-type DNA to the mutant DNA remaining unbound at the end of each cycle. Finally, single-stranded material is amplified by a polymerase chain reaction to generate a probe enriched in sequences missing in the deletion mutant. Of course, this method can only be used to isolate a genomic region that is defined by a deletion mutant, and its applicability to genomes more complicated than that of yeast has not been tested. A similar procedure using biotin-based separation for isolation of differentially expressed cDNAs was described by Lebeau et al., *Nucleic Acids Research* 19: 4778 (1991).

Wieland et al., *Proc. Natl. Acad. Sci. USA* 87: 2720–2724 (1990) described a method for isolating polynucleotides comprising sequences present in a "tester" DNA population that are absent in a "driver" population. In this method, the tester DNA is labeled with biotin, then subjected to several rounds of hybridization with excess driver DNA. After each round, single-stranded DNA is collected by hydroxyapatite chromatography. After the final round, the small amount of nonhybridized biotinylated DNA (unique to the tester population) is purified by avidin affinity chromatography, amplified by a polymerase chain reaction and cloned to generate a probe for sequences unique to the tester population.

Recently, a technique known as Representational Difference Analysis (RDA) has been developed, which allows the isolation of DNA fragments that are present in one population of DNA sequences but absent in another population of DNA sequences. Lisitsyn et al., *Science* 259:946–951 (1993); Lisitsyn et al., *Meth. Enzymology* 254:291–304 (1995); U.S. Pat. No. 5,436,142; U.S. Pat. No. 5,501,964; Lisitsyn et al., *Nature Genetics* 6:57–63 (1994). This method allows one to search for fragments present in a "tester" population of DNA sequences that are not present in a related "driver" population. Such unique fragments are denoted "target" sequences. In the first step of RDA, "representations" of both populations are obtained. These representations consist of lower-complexity subsets of the original sequence populations. In the most widely-practiced embodiment of the technique, a representation is obtained by separately subjecting both populations to digestion with a restriction endonuclease, ligating a first set of adapters to the ends of the fragments so generated, and amplifying by a polymerase chain reaction (PCR) using primers complementary to the first set of adapters, under conditions in which only relatively short fragments (less than 2 kilobase pairs) are amplified. The first adapters are then removed from the amplified fragments of both populations by restriction enzyme digestion and a second set of adapters (having a different sequence than the first set) is attached, by ligation, to amplified fragments from the tester DNA population only.

The adapter-containing amplified fragments from the tester population are then combined with an excess of amplified fragments from the driver population, (which lack adapters) and the mixture is incubated under denaturing and annealing conditions, followed by another round of PCR amplification using primers complementary to the second set of adapters. During the annealing step, several types of duplex will be formed. Because driver fragments are present in excess, the vast majority of fragments containing sequences common to both tester and driver populations will form either driver-driver duplexes (containing no adapter) or tester-driver duplexes (containing a single adapter on the strand derived from the tester fragment). Fragments containing sequences that are unique to the tester population are capable of self-annealing to generate duplexes possessing an adapter at each end. Consequently, during the PCR step subsequent to annealing, tester-tester duplexes will be amplified exponentially. On the other hand, tester-driver duplexes, possessing only a single adapter, will be amplified in a linear fashion and will thus come to form only a small fraction of the population of amplified sequences. Driver-:driver duplexes, lacking adapters, will not be amplified at all. Selective amplification of fragments containing target sequences is thus achieved by virtue of the fact that, prior to annealing, only fragments from the tester population possess adapters, bestowing tester-tester duplexes with the potential for exponential amplification.

The steps of removing the adapters present on the enriched target fragments obtained from a previous step, adding new adapters, incubating under denaturing and annealing conditions with an excess of fragments from the driver population, and amplification by PCR is repeated until a desired degree of enrichment is attained.

An adaptation of RDA called cDNA-RDA has recently been described, Hubank & Schatz *Nucleic Acids Research* 22:5640–5648 (1994), in which two populations of cDNA are compared for the presence a cDNA fragment representing either a mRNA unique to one of the two populations or a mRNA that is differentially expressed in the two populations. cDNA-RDA differs from the original RDA protocol in the following respects. 1) Since the complexity of the mRNA population of a typical mammalian cell is only ~1–2% of genome complexity, generation of a representation is not required for the practice of cDNA-RDA. Hence, a more complete analysis of differences can be obtained in a single experiment. 2) Amplification of fragments already known to differ between the two populations can be minimized by addition of such fragments to the driver. 3) Amplification of fragments representing mRNAs present at different levels in the two populations (rather than absent in one population) can be achieved by depleting the populations of low-abundance sequences (by hybridization to low $C_o t$) prior to amplification, and lowering the ratio of driver to tester during hybridizations subsequent to the generation of the first difference product. This effectively converts an up-regulated sequence into a unique sequence, for the purposes of the assay. A limitation of cDNA-RDA is the inability to detect differences due to point mutations, small deletions or small insertions, unless they affect a particular restriction enzyme recognition site. cDNA-RDA has been used to detect transcripts of a transfected gene in cultured cells and to clone cDNAs representing genes whose transcription is up-regulated in response to an environmental stimulus.

RDA and cDNA-RDA depend upon selective amplification for enrichment of polynucleotides containing sequences unique to, or enriched in, a particular nucleic acid sequence population. Selective amplification of unique sequences was combined with the selective degradation of sequences common to both populations in the technique of enzymatic degrading subtraction. Zeng et al., *Nucleic Acids Research* 22:4381–4385 (1994); U.S. Pat. No. 5,525,471. In this procedure, the ends of the amplified cDNA fragments comprising the tester population are blocked by the enzymatic addition of α-phosphorothioate-modified nucleotides. Hybridization of blocked tester fragments with an excess of unblocked driver fragments is then conducted under conditions that accelerate the annealing rate, allowing the use of relatively low driver concentrations. After hybridization, treatment with exonuclease III (a double strand-specific nuclease which attacks from the 3' end) and exonuclease VII (a single strand-specific nuclease) will destroy driver-driver and tester-driver duplexes. However, the phosphorothioate-blocked ends of tester-tester hybrids will render these duplexes resistant to the combined nuclease treatment. Tester-tester duplexes which survive nuclease treatment undergo a second round of subtraction and are then amplified by a polymerase chain reaction. Additional rounds of subtraction and amplification may be conducted, as necessary.

As the technique of RDA has come to be practiced more widely in recent years, several disadvantages have become apparent. A major problem results from the inefficiency of the multiple restriction digestion and ligation reactions that are utilized in the technique. Lack of complete restriction digestion will lead to incomplete removal of the first set of adapters from the tester fragment population, resulting in an inability to attach the second set of adapters. Similarly, an inefficient ligation step would lead to incomplete attachment of the second set of adapters, even at sites from which the first set had been removed. Since the amplification primers are complementary to the second set of adapters, incomplete attachment of the second adapter set will reduce the degree of amplification of target sequences that can be achieved. In addition, the necessity to process samples through multiple steps, and possibly purify material between steps, leads to losses of already-scarce experimental material. One possible consequence of inefficient restriction digestion and/or ligation is the generation of false positives, wherein the loss of a particular driver sequence, through failure to be amplified, leads to the inappropriate identification of its complement in the tester as a target sequence.

Another disadvantage of RDA as it is commonly practiced stems from the use of a large number of polymerase chain reaction cycles during the amplification step. Typically, 20 cycles of PCR are used to generate the representations and 25–30 cycles of PCR are used during each hybridization/amplification round of RDA. If, as is common, three rounds of hybridization/amplification are conducted, target nucleic acids will have undergone 95–110 rounds of amplification by the time they are isolated. Additional rounds of amplification are commonly used to clone and sequence the difference product isolated by RDA. It has been known for some time that, at high cycle numbers of a PCR amplification, a "plateau effect" is observed. Innis and Gelfland in "PCR Protocols: A guide to methods and applications" ed. Innis et al., Academic Press (1990) pp. 3–12. This effect is characterized by a decline in the exponential rate of accumulation of amplification product that occurs during late cycles. Potential causes of the plateau effect include 1) depletion of substrates, 2) loss of activity of enzyme, 3) degradation of substrates, 4) end-product inhibition, 5) competition for reactants by nonspecific products, 6) incomplete denaturation of product at high product concentration and 7) reannealing of product at high product concentration (which may block primer annealing and/or extension).

These last two features of the later cycles of a polymerase chain reaction are especially important for RDA and related techniques because, besides leading to less-than-exponential amplification, they also result in a skewing of the representation of products in reactions, such as RDA, in which multiple fragments are being amplified. In particular, Mathieu-Daudé et al., *Nucleic Acids Research* 24:2080–2086 (1996) have shown that, in later cycles, the rate of amplification of abundant products decreases more rapidly than that of less abundant products in the same reaction. This is due to preferential reannealing of the more abundant products, which prevents primer binding and/or extension for these abundant species. This phenomenon is consistent with the fact that rate of annealing is proportional to the concentrations of the reacting strands. The consequence of this effect for the practice of cDNA-RDA is that the ability to detect mRNAs present in different concentrations in two populations (as opposed to mRNAs that are unique to one of the populations) will be minimized for mRNAs whose cDNAs are present at high concentrations in the starting population.

A further potential source of artifact in the current procedure for RDA is the utilization of ten cycles of PCR immediately following the first hybridization step. Only after these ten amplification cycles have been conducted is the material treated with nuclease to degrade unhybridized material. This sequence of events has the potentially undesirable effect of subjecting tester:tester duplexes (i.e., the desired product) to ten denaturation steps, with the attendant risk that some of these duplexes will fail to reform, due, for example, to degradation of their constituent strands while in the denatured state.

Finally, the presence of excess driver DNA during the ten PCR cycles prior to nuclease treatment can result in a reduced efficiency of amplification of tester:tester hybrids, due to the potential for the residual driver:driver and driver:tester duplexes to act as a sink for primers, substrates, counterions and enzyme.

In the practice of the present invention, these disadvantages are surmounted by methods that use fewer PCR cycles, nuclease digestion prior to amplification, and a single adapter designed for use with multiple primers. Additional advantages are also presented by the invention, as set forth infra.

SUMMARY OF THE INVENTION

The invention provides improved methods for the identification and isolation of polynucleotides comprising nucleic acid sequences present in a first (sample) cell, cell type, or cell population that are not present in one or more other (control) cell(s), cell type(s) or cell population(s). Such polynucleotides will be identified as "unique fragments" or "difference products," using the methods of the invention. Unique fragments may be obtained as a result of differences in sequence content, such as insertion or deletion, or by differences in sequence organization, such as inversion or translocation. The method of the invention does not suffer from the problems associated with previous methods of subtractive hybridization, such as the losses of material associated with repeated restriction digestion and ligation steps, skewed representations resulting from excessive cycles of amplification, and interference with the amplification steps by large amounts of unwanted control sequences.

Accordingly, the invention provides a method for obtaining a polynucleotide fragment comprising a unique nucleic acid sequence present in a sample population of polynucleotides that is not present in a control population of polynucleotides, said method comprising:

generating a difference product between lower-complexity subsets of a sample population of polynucleotides and a control population of polynucleotides by performing the following steps:

(a) combining said lower-complexity subset of the sample population with an excess of said lower-complexity subset of the control population, denaturing, and incubating under annealing conditions to provide an annealing mixture;

(b) subjecting the annealing mixture to conditions under which members of the lower-complexity subset of the control population will be preferentially degraded or rendered non-amplifiable, compared to members of the lower-complexity subset of the sample population; and (c) subsequently subjecting the annealing mixture treated as in step (b) to amplification, to generate a first difference product.

The invention also provides a method for obtaining additional difference products by repeating the preceding series of steps (a)–(c), wherein the first difference product (or a subsequent difference product) is substituted for the lower-complexity subset of the sample population.

The invention additionally provides a method for generating lower-complexity subsets of sample and control populations of polynucleotides by performing the following series of steps:

a) fragmenting both populations of polynucleotides by the same method to generate sample and control fragment populations;

b) differentially marking said sample and control fragment populations to generate a marked sample fragment population and a marked control fragment population, such that the marked control fragment population becomes selectively susceptible to degradation, compared to the marked sample fragment population; and c) amplifying the marked sample and control fragment populations under conditions wherein the degree of amplification is limited to generate lower-complexity subsets of the marked sample and control fragment populations.

The invention further provides a method for obtaining a polynucleotide fragment comprising a unique nucleic acid sequence present in a sample population of polynucleotides that is not present in a control population of polynucleotides, said method comprising:

a) generating lower-complexity subsets of said populations by performing the following series of steps:

(i) fragmenting both populations of polynucleotides by the same method to generate sample and control fragment populations;

(ii) differentially marking said sample and control fragment populations to generate a marked sample fragment population and a marked control fragment population, such that the marked control fragment population becomes selectively susceptible to degradation, compared to the marked sample fragment population;

(iii) amplifying the marked sample and control fragment populations under conditions wherein the degree of amplification is limited to generate lower-complexity subsets of the marked sample and control fragment populations; and b) generating a difference product by performing the following series of steps:

(i) combining said lower-complexity subset of the marked sample fragment population with an excess of said lower-complexity subset of the marked control fragment population, denaturing, and incubating under annealing conditions to provide an annealing mixture;

(ii) subjecting the annealing mixture to conditions under which members of the lower-complexity subset of the marked control fragment population will be preferentially degraded or rendered non-amplifiable, compared to members of the lower-complexity subset of the marked sample fragment population; and (iii) subsequently subjecting the annealing mixture treated as in step (ii) to amplification, to generate a first difference product.

The invention also provides a method for obtaining additional difference products by repeating the preceding series of steps (b), wherein the first difference product (or a subsequent difference product) is substituted for the lower-complexity subset of the marked sample fragment population.

The invention further provides a method for obtaining a polynucleotide fragment comprising a unique nucleic acid sequence present in a sample population of polynucleotides that is not present in a control population of polynucleotides, said method comprising:

a) fragmenting both populations of polynucleotides by the same method to generate sample and control fragment populations;

b) differentially marking said sample and control fragment populations to generate a marked sample fragment population and a marked control fragment population, such that the marked control fragment population becomes selectively susceptible to degradation, compared to the marked sample fragment population; and c) generating a difference product by performing the following series of steps:

(i) combining said marked sample fragment population with an excess of said marked control fragment population, denaturing, and incubating under annealing conditions to provide an annealing mixture;

(ii) subjecting the annealing mixture to conditions under which members of the marked control fragment population will either be preferentially degraded or rendered non-amplifiable, compared to members of the marked sample fragment population;

(iii) subsequently subjecting the annealing mixture treated as in step (ii) to amplification, to generate a first difference product.

The invention also provides a method for obtaining additional difference products by repeating the preceding series of steps (c), wherein the first difference product (or a subsequent difference product) is substituted for the marked sample fragment population.

The invention additionally provides a method for obtaining a polynucleotide fragment comprising a unique nucleic acid sequence present in a sample population of polynucleotides that is not present in a control population of polynucleotides, said method comprising:

a) generating lower-complexity subsets of said populations by performing the following series of steps:

(i) fragmenting both populations of polynucleotides by the same method to generate sample and control fragment populations;

(ii) covalently attaching to both fragment populations an oligonucleotide comprising nested primer binding sites, said primer binding sites comprising an outermost primer binding site, an innermost primer binding site, and at least one more internal primer binding site therebetween, to produce marked sample and control fragment populations;

(iii) amplifying the marked sample fragment population under conditions wherein the degree of amplification is limited, using a non-targeting primer complementary to the outermost primer binding site of said oligonucleotide to generate a lower-complexity subset of the sample fragment population; and (iv) amplifying the marked control fragment population under conditions wherein the degree of amplification is limited, using a targeting primer complementary to the innermost primer binding site of said oligonucleotide to generate a lower-complexity subset of the control fragment population; and b) generating a difference product by performing the following series of steps:

(i) combining the lower-complexity subset of said sample fragment population with an excess of the lower-complexity subset said control fragment population, denaturing, and incubating under annealing conditions to provide an annealing mixture;

(ii) subjecting the annealing mixture to conditions under which all fragments will be degraded, except for double-stranded fragments containing a non-targeting primer in each strand; and (iii) subsequently subjecting the annealing mixture to amplification, using non-targeting primers complementary to one of said internal primer binding sites, to generate a first difference product.

The invention also provides a method for obtaining additional difference products by repeating the preceding series of steps (b), wherein the first difference product (or a subsequent difference product) is substituted for the lower-complexity subset of the sample fragment population, and wherein the treated annealing mixture is subjected to amplification using a non-targeting primer complementary to an internal primer binding site different from that used in the preceding step or a non-targeting primer complementary to the innermost primer binding site.

The invention additionally provides a method for obtaining a unique fragment present in a sample population of polynucleotides that is not present in a control population of polynucleotides, said method comprising:

a) obtaining fragments of both populations of polynucleotides to provide a sample fragment population and a control fragment population;

b) amplifying said sample and control fragment populations to provide an amplified sample fragment population and an amplified control fragment population;

c) combining said amplified sample fragment population with an excess of said amplified control fragment population, denaturing, and incubating under annealing conditions to provide an annealing mixture;

d) subjecting the annealing mixture to conditions under which members of the amplified control fragment population will be preferentially degraded or rendered non-amplifiable, compared to members of the amplified sample fragment population; and e) subsequently subjecting the annealing mixture treated as in step (d) to amplification, to generate a first difference product.

The invention also provides a method for obtaining additional difference products by repeating the preceding series of steps (c) - (e), wherein the first difference product (or a subsequent difference product) is substituted for the amplified sample fragment population.

The invention additionally provides a method for obtaining a unique fragment present in a sample population of polynucleotides that is not present in a control population of polynucleotides, said method comprising:

a) fragmenting both populations of polynucleotides by the same method to generate sample and control fragment populations;

b) differentially marking said sample and control fragment populations to generate a marked sample fragment population and a marked control fragment population, such that the marked control fragment population becomes selectively susceptible to degradation, compared to the marked sample fragment population;

c) amplifying the marked sample and control fragment populations to generate an amplified, marked sample fragment population and an amplified, marked control fragment population;

d) combining said amplified, marked sample fragment population with an excess of said amplified, marked control fragment population, denaturing, and incubating under annealing conditions to provide an annealing mixture;

e) subjecting the annealing mixture to conditions under which members of the amplified, marked control fragment population will be preferentially degraded or rendered non-amplifiable, compared to members of the amplified, marked sample fragment population; and f) subsequently subjecting the annealing mixture treated as in step (e) to amplification, to generate a first difference product.

The invention also provides a method for obtaining additional difference products by repeating the preceding series of steps (d) through (f), wherein the first difference product (or a subsequent difference product) is substituted for the amplified, marked sample fragment population, to provide additional difference products.

The invention additionally provides a method for obtaining a unique fragment present in a sample population of polynucleotides that is not present in a control population of polynucleotides, said method comprising:

a) fragmenting both populations of polynucleotides by the same method to generate sample and control fragment populations;

b) covalently attaching to both fragment populations an oligonucleotide containing or encoding nested primer binding sites, said primer binding sites comprising an outermost primer binding site, an innermost primer binding site, and at least one more internal primer binding site therebetween, to produce oligonucleotide-labeled sample and control fragment populations;

c) amplifying the oligonucleotide-labeled sample fragment population, using a non-targeting primer complementary to the outermost primer binding site of said oligonucleotide to generate an amplified sample fragment population; and d) amplifying the oligonucleotide-labeled control fragment population, using a targeting primer complementary to the innermost primer binding site of said oligonucleotide to generate an amplified control fragment population;

e) combining said amplified sample fragment population with an excess of said amplified control fragment population, denaturing, and incubating under annealing conditions to provide an annealing mixture;

f) subjecting the annealing mixture to conditions under which all fragments will be degraded, except for double-stranded fragments containing a non-targeting primer in each strand; and g) subsequently subjecting the annealing mixture treated as in step (f) to amplification, using non-targeting primers complementary to one of said internal primer binding sites, to generate a first difference product.

The invention also provides a method for obtaining additional difference products by repeating the preceding series of steps (e) through (g), wherein the first difference product (or a subsequent difference product) is substituted for the amplified sample fragment population, and wherein the treated annealing mixture is subjected to amplification using a non-targeting primer complementary to an internal primer binding site different from that used in the preceding step or a non-targeting primer complementary to the innermost primer binding site, to provide additional difference products.

The invention additionally provides a method for obtaining a polynucleotide fragment comprising a unique nucleic acid sequence present in a sample population of polynucleotides that is not present in a control population of polynucleotides, said method comprising:

a) fragmenting both populations of polynucleotides by the same method to generate sample and control fragment populations;

b) covalently attaching to both fragment populations an oligonucleotide comprising nested primer binding sites or the complements thereof, said primer binding sites comprising an outermost primer binding site, an innermost primer binding site, and at least one more internal primer binding site therebetween, to produce marked sample and control fragment populations;

c) amplifying the marked sample fragment population using a non-targeting primer complementary to the outermost primer binding site of said oligonucleotide to generate an amplified sample fragment population; and d) amplifying the marked control fragment population using a targeting primer complementary to the innermost primer binding site of said oligonucleotide to generate an amplified control fragment population; and e) generating a difference product by performing the following series of steps:

(i) combining said amplified sample fragment population with an excess of said amplified control fragment population, denaturing, and incubating under annealing conditions to provide an annealing mixture;

(ii) subjecting the annealing mixture to conditions under which all fragments will be degraded, except for double-stranded fragments containing a non-targeting primer in each strand;

(iii) subsequently subjecting the annealing mixture to amplification, using non-targeting primers complementary to one of said internal primer binding sites, to generate a first difference product.

The invention also provides a method for obtaining additional difference products by repeating the preceding series of steps (e), wherein the first difference product (or a subsequent difference product) is substituted for the amplified sample fragment population, and wherein the treated annealing mixture is subjected to amplification using a non-targeting primer complementary to an internal primer binding site different from that used in the preceding step or a non-targeting primer complementary to the innermost primer binding site.

In a preferred embodiment, methods for obtaining unique cDNA fragments, representative of differences in the mRNA population of two or more different cells, cell types or cell populations are provided.

In another embodiment, methods for obtaining a difference product, comprising one or more polynucleotide fragments that differ between two polynucleotide populations, are provided.

In another embodiment, methods for obtaining fragments representing sequence differences between two genomes are provided.

In another embodiment, methods for obtaining cDNAs representing RNA molecules that are unique to a particular polynucleotide population are provided.

In another embodiment, methods for obtaining cDNAs representing RNA molecules that are preferentially expressed in a particular polynucleotide population are provided.

In another embodiment, an improved method of representational difference analysis is provided, in which multiple steps of restriction digestion and ligation are avoided.

In another embodiment, a method of targeting a population of polynucleotides for selective degradation is provided.

In another embodiment, a method of achieving selective amplification of a population of polynucleotides is provided.

In another embodiment, an oligonucleotide having multiple primer binding sites for use in the method of the invention and related methods is provided.

In another embodiment, an oligonucleotide having multiple primer binding sites with increasing annealing temperatures from the 5'- to the 3'-end, for use in the method of the invention and related methods, is provided.

DETAILED DESCRIPTION OF THE INVENTION

Figure 1:
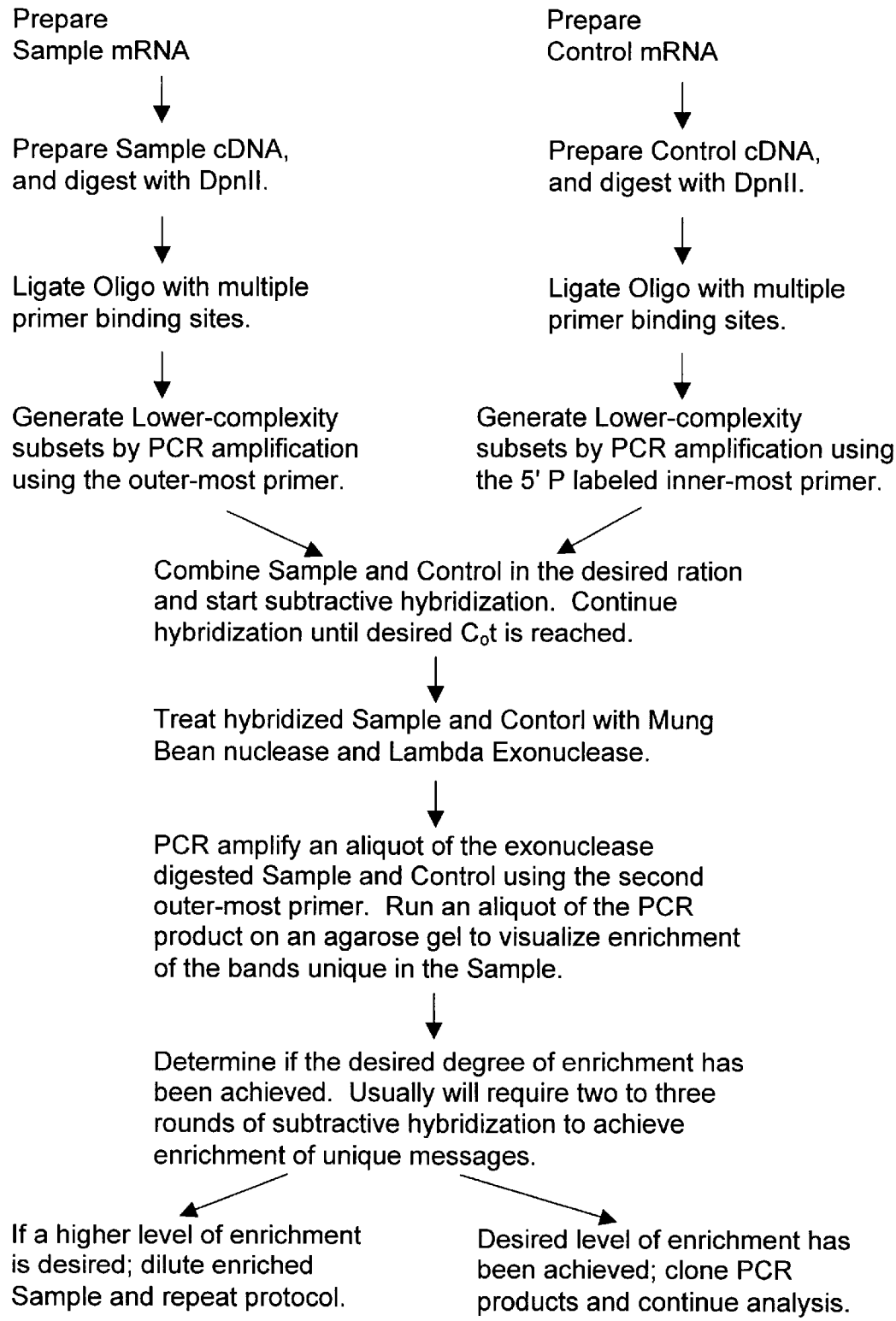
FIG. 1 shows a flow chart for a preferred embodiment of the method of the invention.

The present invention provides improved methods for subtractive hybridization to identify polynucleotide fragments that are unique to a particular sample population of polynucleotides. The method can be used to isolate, among other things, polynucleotide fragments such as cDNAs, that are characteristic of a particular pathological or developmental state. The method is quicker than existing methods, provides a higher yield of authentic product, and generates a more representative collection of unique fragments than do previous methods.

Unless otherwise indicated, the practice of the present invention will employ conventional techniques of molecular biology, biochemistry, microbiology, recombinant DNA, nucleic acid hybridization, genetics, immunology, embryology and oncology which are within the skill of the art. Such techniques are explained fully in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Glover, DNA CLONING: A PRACTICAL APPROACH, volumes I and II, IRL Press (1985), volume III, IRL Press (1987); Perbal, A PRACTICAL GUIDE TO MOLECULAR CLONING, John Wiley & Sons (1984); Rigby (ed.), The series GENETIC ENGINEERING (Academic Press); Setlow & Hollaender (eds.), The series GENETIC ENGINEERING: PRINCIPLES AND METHODS, Plenum Press; The series METHODS IN ENZYMOLOGY (Academic Press); Silhavy, Berman & Enquist, EXPERIMENTS WITH GENE FUSIONS, Cold Spring Harbor Laboratory Press (1984); Gait (ed.), OLIGONUCLEOTIDE SYNTHESIS: A PRACTICAL APPROACH, IRL Press (1984, 1985); Eckstein (ed.) OLIGONUCLEOTIDES AND ANALOGUES: A PRACTICAL APPROACH, IRL Press (1991); Hames & Higgins, NUCLEIC ACID HYBRIDIZATION: A PRACTICAL APPROACH, IRL Press (1985); Hames & Higgins, TRANSCRIPTION AND TRANSLATION: A PRACTICAL APPROACH, IRL Press (1984); Freshney, ANIMAL CELL CULTURE: A PRACTICAL APPROACH, IRL Press (1986); Mahy, VIROLOGY: A PRACTICAL APPROACH, IRL Press (1985); Woodward, IMMOBILIZED CELLS AND ENZYMES: A PRACTICAL APPROACH, IRL Press (1985); Miller & Calos (eds.), GENE TRANSFER VECTORS FOR MAMMALIAN CELLS, Cold Spring Harbor Laboratory Press (1987); Erlich (ed.) PCR TECHNOLOGY, Stockton Press (1989); Innis et al., PCR PROTOCOLS, Academic Press (1990). All patents and publications mentioned herein, both supra and infra, are hereby incorporated herein by reference.

In describing the present invention, the following terminology, as defined below, will be used.

A polynucleotide is a polymer of nucleotides, and the term is meant to embrace smaller polynucleotides (fragments) generated by fragmentation of larger polynucleotides. The terms polynucleotide and nucleic acid encompass both RNA and DNA, as well as single-stranded and double-stranded polynucleotides and nucleic acids. Polynucleotides also include modified polynucleotides and nucleic acids, containing such modifications of the base, sugar or phosphate groups as are known in the art.

A population of polynucleotides is any collection of polynucleotides comprised of different nucleotide sequences. Examples of polynucleotide populations include, but are not limited to, the genome of a normal cell, the genome of an infected cell, the genome of a neoplastic cell, the genome of a cell existing in a pathological state, the DNA that is characteristic of a particular cell, multicellular structure, organism, state of differentiation, pathological or non-pathological state, the total RNA population of a cell, the polyadenylated RNA population of a cell, or a cDNA population representative of the mRNA population of a particular cell, multicellular structure, organism, state of differentiation, pathological or non-pathological state.

Using the methods of this invention, one will search a sample population of polynucleotides for fragments comprising one or more polynucleotide sequences that are unique with respect to a control population of polynucleotides. A sample population will be obtained, for example, from a particular cell, cell type, infected cell, pathological cell, or cells at a particular state of development or disease progression, and tested for the presence of one or more unique fragments by comparison to a control population, according to the methods of the invention. By way of example, if a sample population is obtained from virusinfected cells, the control population would be obtained from uninfected cells of the same type. In certain situations, such as identification of a sequence that is deleted in a particular pathological state, normal (non-pathological) cells may be used as the sample population.

Sequence complexity or complexity is defined as the length of non-repeated nucleotide sequence present in a population of polynucleotides.

A lower-complexity subset of a population of polynucleotides or fragments is a collection which contains some, but not all of the sequences or fragments present in the original population.

A fragment of a nucleic acid is a smaller piece of that nucleic acid. Fragmentation is the process by which fragments are obtained. Fragmentation can be achieved by any method known in the art; for example, enzymatically, chemically, mechanically, etc., provided the method reproducibly generates the same set of fragments for a given population of polynucleotides. One common method of fragmentation of a polynucleotide population is to subject the population to the action of a restriction endonuclease.

A fragment population is obtained when a nucleic acid or a population of polynucleotides is subjected to fragmentation.

As used herein, marking refers to a method by which additional sequences are added to a polynucleotide or nucleic acid fragment. A marked population of polynucleotide fragments may be generated, for example, by the attachment of oligonucleotide linkers or adapters to a population of polynucleotide fragments. Differential marking refers to a situation in which the presence of the additional sequences is exploited to distinguish two or more populations of polynucleotides or polynucleotide fragments from one another.

Denaturation refers to the process by which a double-stranded nucleic acid is converted into its constituent single strands. Denaturation can be achieved, for example, by the use of high temperature, low ionic strength, acidic or alkaline pH, and/or certain organic solvents. Methods for denaturing nucleic acids are well-known in the art.

Annealing (sometimes called hybridization) refers to the process by which complementary single-stranded nucleic acids form a double-stranded structure, or duplex, mediated by hydrogen-bonding between complementary bases in the two strands.

Annealing conditions are those values of, for example, temperature, ionic strength, pH and solvent which will allow annealing to occur. Many different combinations of the above-mentioned variables will be conducive to annealing. Appropriate conditions for annealing are well-known in the art, and will generally include an ionic strength of 50 mM or higher monovalent and/or divalent cation at neutral or near-neutral pH.

An annealing mixture is a composition containing single-stranded nucleic acid at the appropriate temperature, pH and ionic strength to allow annealing to occur between molecules sharing regions of complementary sequence.

A duplex refers to a double-stranded polynucleotide.

Amplification is the process by which additional copies of a nucleic acid sequence or collection of nucleic acid sequences are generated. Amplification is generally achieved enzymatically, using a DNA polymerase enzyme. Current techniques allow exponential amplification of any sequence flanked by binding sites for a pair of oligonucleotide primers, through reiterative application of denaturation, primer annealing and polymerase extension steps, commonly known as a polymerase chain reaction. U.S. Pat. No. 4,683,202, Saiki et al., Science 239:487–491 (1988), Innis et al., supra, Erlich, supra. Under the most widely-practiced conditions of the polymerase chain reaction, the rate of polymerization is approximately 1,000–2,000 nucleotides per minute. Accordingly, the maximum length of amplifiable sequence will be limited by the reaction conditions (for example, the duration of the extension step). The ability to control the extent of elongation in a polymerase chain reaction can be used to advantage to generate lower-complexity subsets of amplified fragments from an initial fragment collection of high complexity.

Degradation refers to the depolymerization of a polynucleotide. Degradation of a polynucleotide will generally occur through hydrolysis of internucleotide phosphodiester bonds to release short oligonucleotides and/or mononucleotides. Degradation may be achieved either chemically or enzymatically. In a preferred embodiment of the present invention, fragments of a control population of polynucleotide fragments will undergo preferential exonucleolytic degradation due to their being differentially marked compared to a sample population of polynucleotide fragments.

A difference product is a polynucleotide obtained as a result of the practice of the present invention. It will contain one or more polynucleotides or polynucleotide fragments that are present in a sample population of polynucleotides or polynucleotide fragments which are not present in a control population of polynucleotides or polynucleotide fragments.

A unique fragment is a fragment that is present in a sample population of polynucleotides or polynucleotide fragments which is not present in a control population of polynucleotides or polynucleotide fragments.

A primer is an oligonucleotide capable of base-pairing with a polynucleotide and serving as a site from which polymerization can be initiated.

A primer having properties such that its extension product will be susceptible to degradation is known as a targeting primer; a primer having properties such that its extension product is protected from degradation is known as a non-targeting primer. More generally, a targeted population of polynucleotides is one that is preferentially susceptible to degradation by virtue of some unique property or constituent that is not shared with a non-targeted population of polynucleotides.

A primer binding site refers to a region of a polynucleotide, such as an adapter or a sequence encoded by an adapter, that is capable of base-pairing with a primer, or that encodes a sequence that is able to base-pair with a primer. By way of example, the adapters of the present invention may contain within their sequence or encode multiple primer binding sites. In the case of multiple primer binding sites, the outermost primer binding site is the primer binding site located closest to the 3' end of the nucleic acid strand in which it resides. The innermost primer binding site is located farthest from the 3' end of the nucleic acid strand in which it resides. One or more internal primer binding site(s) may be present between the outermost and innermost primer binding sites. It should be noted that, since polymerization proceeds in a 5'-to-3' direction and a primer binding site is complementary to the primer from which polymerization is initiated, an outermost primer binding site encodes a sequence closest to the 5'-end of the product of polymerization, compared to internal or innermost primer binding sites.

An oligonucleotide is a short nucleic acid, generally DNA and generally single-stranded. Generally, an oligonucleotide will be shorter than 200 nucleotides, more particularly, shorter than 100 nucleotides, most particularly, 50 nucleotides or shorter.

A nuclease is an enzyme capable of degrading nucleic acids. An exonuclease degrades from the ends of a nucleic acid molecule. A 5'-specific exonuclease will begin degradation at the 5' end of a nucleic acid molecule, and a 3'-specific exonuclease will begin degradation at the 3' end of a nucleic acid molecule. 5'-specific exonucleases may additionally be specific for either 5'-phosphate- or 5'-hydroxyl terminated ends. Similarly, 3'-specific exonucleases may be specific for either 3'-phosphate- or 3'-hydroxyl terminated ends. An endonuclease degrades internally in a nucleic acid molecule. A single strand-specific nuclease is capable of degrading single-stranded nucleic acids, either exonucleolytically or endonucleolytically, but is unable to degrade a double-stranded nucleic acid.

Genomic DNA is DNA obtained from a cell representing all or part of the genome of that cell.

cDNA or "complementary DNA" is DNA obtained from copying RNA by reverse transcription. It most often represents the population of mRNA molecules found in a particular cell, cell type, state of development or pathological state.

METHOD OF THE INVENTION

A. Starting Material

The starting material for the practice of the method of the invention will be at least two populations of polynucleotides. A population of polynucleotides may comprise the genome of a cell or group of cells and may be obtained, for example, by techniques known in the art such as disruption of cells, optionally followed by isolation of nuclei. The preparations of disrupted cells or nuclei may be further subjected to the actions of proteolytic enzymes and extraction with organic solvents, and nucleic acids may be purified by any of several methods known in the art, including chromatography and selective precipitation.

Alternatively, populations of cDNA may be used as starting material for the practice of the method of the invention. In this instance, RNA will first be purified from the cell, cell type or cell population of interest, taking appropriate precautions, as are known in the art, to minimize degradation of RNA. Polyadenylated RNA, mRNA, cytoplasmic RNA, total cellular RNA or other selected RNA populations may be used. Said RNA will be converted into cDNA ("complementary DNA") by, for instance, the sequential actions of a reverse transcriptase enzyme to generate a first strand and a DNA polymerase to convert the first strand to a duplex, by methods well-known in the art (see, for example, Maniatis et al., Sambrook et al., Ausubel et al., supra).

Other types of nucleic acids or polynucleotides, as contemplated by the art, may also be used as starting material.

B. Fragmentation and optional selection of lower-complexity subsets

To facilitate the process of amplification, the polynucleotide populations are subjected to fragmentation. Fragmentation may be achieved by digestion of nucleic acids with a restriction endonuclease, for example. Other methods of fragmentation may include digestion with a single-strand-specific nuclease such as Mung Bean Nuclease or SI Nuclease at temperatures intermediate between physiological temperature and the melting temperature of the polynucleotide to be fragmented. Under certain conditions, fragmentation by mechanical shear might also be adequate.

For polynucleotide populations of high complexity, for example the genome of a human cell, methods for reducing the complexity of said polynucleotide population may optionally be employed. For example, fragmentation of a polynucleotide or population of polynucleotides using a method which reproducibly generates the same set of fragments can be used as a first step in obtaining a lower-complexity subset of the starting population of polynucleotides. Following fragmentation, selection of a subset of the fragments so generated will provide one with a subset of the original population of polynucleotides, having a lower complexity than that of the starting material, if such is desired. Selection may be achieved, for example, by size. Size selection can be accomplished by many methods that are known in the art, for example, gel electrophoresis and column chromatography. A preferred method for achieving size selection is to digest a population of polynucleotides with a restriction enzyme. If the polynucleotide population originates from genomic DNA, a restriction enzyme having a six-nucleotide recognition sequence is often used. The population of fragments generated by restriction enzyme digestion is then subjected to amplification, for example by PCR, under conditions in which the size of the amplification product is limited to less than approximately 2 kilobases; such conditions being known in the art (Innis et al., supra). Since a portion of the fragments generated by digestion with a restriction enzyme having a six-nucleotide recognition sequence will be larger than approximately 2 kilobases, they will not be amplified. Hence, the amplified population will contain a subset of the starting fragment population.

Selection may be achieved by other art-recognized methods in addition to size. For example, buoyant density, sequence composition and affinity for a particular ligand are non-limiting examples of additional selection techniques.

Certain nucleic acid populations, such as those representing the mRNA population of a cell, may be of sufficiently low complexity that the generation of a lower-complexity subset may not be necessary. In this case, digestion with a restriction enzyme having a four-nucleotide recognition sequence will facilitate the subsequent attachment of adapters to provide an amplified fragment population for use in the annealing step and lead to amplification of virtually all fragments (since the majority of fragments produced by cleavage with a restriction enzyme having a four-nucleotide recognition sequence will be shorter than 2 kilobases).

C. Adapter oligonucleotides

The present invention provides novel adapter oligonucleotides, whose use leads to greater efficiency and higher yields of authentic difference product, by obviating the necessity for repeated replacement of adapters by restriction enzyme digestion and ligation. These novel adapter oligonucleotides contain or encode binding sites for several individual primers, which may be used for fragment amplification and, if desired, to target certain of the resultant amplified fragments for selective degradation. The novel oligonucleotides are of sufficient length so as to contain several primer binding sites, but not so long as to interfere with the specificity of hybridization (i.e., by containing regions of self-complementarity). The multiple primer binding sites contained within or encoded by an adapter may overlap one another to generate nested primer binding sites, or the primer binding sites may be discrete.

In a preferred embodiment, each sequence encoding a primer binding site, progressing from the 5' end to the 3' end of the adapter will have a successively higher annealing temperature. The difference in annealing temperature between adjacent sites will be approximately 10° C., more preferably 5° C. and, most preferably, 3° C. Consequently, the guanine+cytosine content and/or the length of each primer binding site will also increase, in progressing from the 5' end to the 3' end of the adapter. Thus, in general, the 5'-most, or outermost primer binding site will be shorter, have a lower guanine+cytosine content, and a lower annealing temperature, while the 3'-most, or innermost primer binding site will be longer, have a higher guanine+cytosine content, and a higher annealing temperature. The range of annealing temperatures for the individual primer binding sites of the adapter should, at the low end, be sufficiently high to allow specific hybridization and, at the high end, not be inhibitory to the DNA polymerase used for amplification. This range will be from about 20° C. to 90° C., more preferably from about 35° C. to about 85° C., still more preferably between about 45° C. to about 80° C. and most preferably from about 55° C. to about 75° C. In a preferred embodiment, the oligonucleotide adapter contains four primer binding sites. However, it is clear that more or less than four primer binding sites would also be encompassed by the invention, and that there need not necessarily be any specific relationship among the annealing temperatures of the primer binding sites.

The adapters are attached to fragments by techniques that are well-known in the art. Adapters may be attached chemically or enzymatically, via the action of a DNA or RNA ligase (e.g., see Maniatis et al., Sambrook et al., Ausubel et al., supra). In a preferred method for attachment of adapters, fragmentation of a DNA population will be achieved by treatment with a restriction enzyme that leaves a 5'-protruding end. A short oligonucleotide, part of which is complementary to this 5'-overhang and part of which is complementary to the sequence at the 3'-end of the adapter is used to align the adapter for attachment of the 3'-terminus of the adapter to the 5'-terminus of the restriction enzyme-generated end. After attachment of the adapter, the short oligonucleotide is removed by denaturation and the complement of the adapter is synthesized by the action of a DNA polymerase, using the 3' end of the original fragment as a primer.

If lower-complexity subsets of the control and sample polynucleotide populations are to be generated by selective amplification of small fragments, adapters are attached to the members of the population prior to this step; and it is preferred that the sample fragment population is amplified using a non-phosphorylated primer complementary to the outermost primer binding site, while the control fragment population is amplified using a phosphorylated primer complementary to the innermost primer binding site.

D. Generation of differentially-marked control and sample fragment populations

After attachment of adapters, the control and sample fragment populations are separately subjected to an initial amplification step, preferably by a polymerase chain reaction. Generation of the complement of the adapter sequence, as just described, can be accomplished prior to the initial amplification by conducting an initial extension in the absence of primer.

Through the process of this initial amplification step, the amplification products of the sample and control fragment populations will become differentially marked. This differential marking will target the amplified fragments of the control population for selective degradation, and insure that non-targeted duplexes (arising during subsequent annealing steps) from the amplified fragments of the sample population are resistant to degradation. Differential marking is accomplished by using different types of primers for amplification of the control fragment population and the sample fragment population, as will now be described.

Primers capable of annealing to the primer binding sites of the oligonucleotide adapter may be either phosphorylated or non-phosphorylated at their 5' end. It is within the skill of the art to prepare either type of primer by automated synthesis (see, e.g., Applied Biosystems Model 380D DNA synthesizer User's Manual and associated technical reports, Gait, supra, and Eckstein, supra, the disclosures of which are hereby incorporated by reference). Phosphorylated oligonucleotides are synthesized on an automated instrument by using a phosphorylated monomer in the final coupling cycle. Such a phosphorylated monomer for use in automated synthesis may be obtained commercially, for example from Clontech Laboratories, Palo Alto, Calif. or Applied Biosystems, Foster City, Calif. or Glen Research, Sterling, Va. or other commercial vendors. Alternatively, a phosphorylated oligonucleotide may be prepared through automated synthesis of a 5'-hydroxyl-terminated oligonucleotide, followed by enzymatic phosphorylation using methods well-known in the art (e.g. Maniatis et al., Sambrook et al., Ausubel et al., supra).

In a preferred embodiment of the present invention, phosphorylated and non-phosphorylated primers will be used in the differential marking of two populations of polynucleotide fragments, as follows. In the initial amplification of the control fragment population, a 5'-phosphorylated primer is used for amplification. In the initial amplification of the sample population, a 5'-non-phosphorylated primer is used for amplification. The presence of a 5'-phosphate group on fragments comprising the amplified control fragment population renders those fragments susceptible to the action of nucleases which initiate exonucleolytic degradation at 5'-phosphate-termini, such as λ exonuclease. By contrast, lack of a 5'-phosphate on fragments comprising the sample fragment population protects these fragments from the action of 5'-phosphate-specific nucleases such as X exonuclease. A primer whose extension products are susceptible to degradation is known as a targeting primer and its extension products are said to be targeted; while a primer whose extension products are protected from degradation is known as a non-targeting primer and its extension products are said to be non-targeted. Other types of non-targeting primer include those containing one or more a-phosphorothioate or methyl phosphonate internucleotide linkages near the 5' end, or primers whose 5'-end is blocked with amine or thiol groups, all of which also yield extension products that are resistant to degradation by λ exonuclease. Other types of 5' end modification [i.e., modified nucleic acid structures such as, for example, bicyclo DNA, Bolli et al. (1996) *Nucleic acids Res.* 24: 4660–4667, and peptide nucleic acids, Nielsen et al. (1991) *Science* 254:1497–1500] which render an oligo- or polynucleotide resistant to a 5'-specific exonuclease are also contemplated by the invention. In addition, other types of nuclease can be used for degradation of targeted nucleic acid strands. For example, T7 gene 6 exonuclease is a double strand-specific exonuclease that hydrolyzes in a 5'-to-3' direction. Kerr and Sadowski (1989) *J. Biol. Chem.* 247:311–318. However, digestion by T7 gene 6 exonuclease can be blocked by the presence of four or more phosphorothioate bonds at the 5' end of a double-stranded DNA molecule. Nikiforov et al. (1994) *PCR Meth. & App.* 3:285–291. Monomers and reagents useful for the incorporation of amino- or thio-modified nucleotides during automated oligonucleotide synthesis are available from various commercial suppliers, for example Clontech Laboratories, Palo Alto, Calif. or Applied Biosystems, Foster City, Calif. or Glen Research, Sterling, Va., or other suppliers.

For the production of non-targeted amplification products, amplification is primed with a 5' hydroxyl-terminated primer complementary to a primer binding site different from the one used for amplification of the targeted fragment population. Generally, the amplified control fragment population will be targeted and the amplified sample fragment population will be non-targeted.

Another method of targeting the lower-complexity subset of a control fragment population is to grow the cells from which the control population is to be derived under conditions where uracil is incorporated into the DNA in place of thymine (or perform the initial amplification of the control fragment population using deoxyuridine triphosphate in place of thymidine triphosphate). This would render the uracil-substituted DNA susceptible to the degradative action of the enzyme uracil-DNA-glycosylase.

In the most preferred embodiment of the initial amplification step of the invention, the control fragment population will be amplified using a phosphorylated primer having a sequence complementary to the innermost primer binding site of the adapter, and the sample fragment population will be amplified using a non-phosphorylated primer having a sequence complementary to the outermost primer binding site of the adapter.

E. Annealing

The differentially marked control and sample fragment populations, generated by the initial amplification reactions, are combined with each other, subjected to denaturation conditions, then incubated under annealing conditions, with fragments from the control population in excess. This excess (with respect to moles of nucleotide) may range from 2:1 to 100,000:1, depending upon the requirements of the experiment, and is preferably 100:1. The excess of control to sample fragments may be different for the different hybridization/amplification cycles.

Conditions promoting denaturation, including high temperature and/or low ionic strength and/or moderate-to-high concentration of organic solvent, are well-known in the art. Similarly, conditions promoting reannealing or renaturation, such as high ionic strength and/or lower temperatures, and the variation of these conditions to adjust the stringency of hybridization, are well-known in the art (e.g., Maniatis et al., Sambrook et al., Ausubel et al., supra). The time of annealing can be varied depending on the complexity of the sequences in the reaction and the extent of renaturation desired, and is generally determined by use of the formula:

$$C_o t_{1/2} = 1/k.$$

where $C_o$ refers to the initial concentration of single-stranded DNA, $t_{1/2}$ is the time at which half of the starting single-stranded DNA has formed duplex, and k is the rate constant of reassociation, which depends upon the complexity of the DNA population. Annealing mixtures are generally buffered near neutral pH and may also contain chelating agents, such as EDTA. See Sambrook et al. supra, Ausubel et al. supra and Hames & Higgins (1985) supra, for example.

The ionic strength of an annealing mixture is traditionally adjusted using the $Na^+$ cation. However, the $Mg^{2+}$ cation would be preferable for several reasons. First, a given concentration of $Mg^{2+}$ will provide correspondingly higher ionic strength, compared to an equal concentration of a monovalent cation such as $Na^+$ or $K^+$. Second, the high concentration of $Na^+$ used in annealing reactions (typically approximately 1 M) is inhibitory to the DNA polymerase enzymes used for amplification, and is too high to allow dilution of the annealing mixture into the amplification reaction while maintaining reasonable reaction volumes, necessitating precipitation or purification of the annealed product prior to amplification. Heretofore, the use of $Mg^{2+}$ in annealing reactions was precluded by the frequent presence of $Mg^{2+}$ dependent nucleases which often contaminated preparations of DNA and RNA. In the present invention, nucleic acids to be amplified have generally been subjected to a sufficient number of purification steps (e.g., before and after ligation of adapters) that nuclease contamination is negligible. Alternatively, nucleic acid preparations can be purified by chromatography on specially-designed matrices, such as Qiaex II (Qiagen) or GeneClean (Bio 101) to yield nuclease-free preparations. Consequently, the present invention contemplates the use of $Mg^{2+}$ in the annealing reaction at a concentration of 62.5 mM, which is equivalent to 1 M NaCl in terms of ionic strength. Wetmur and Sninsky in "PCR Strategies" ed. Innis et al., Academic Press (1995). pp.69–83. After the annealing reaction is complete, the reaction mixture may simply be diluted into the components of the amplification reaction such that the $Mg^{2+}$ concentration is between 1–5 mM, depending upon the $Mg^{2+}$ optimum of the DNA polymerase used for amplification, which is generally about 1.5 mM.

F. Nuclease digestion

After annealing, the annealing mixture is treated such that targeted fragments are degraded and non-targeted fragments are both protected from degradation and preferentially amplified. The meanings of the terms "targeted" and "non-targeted" and the methods by which selective degradation of targeted fragments and selective amplification of non-targeted fragments is achieved have been described supra.

Accordingly, the annealing step is followed by one or more nuclease digestion steps, in which targeted polynucleotides are susceptible to degradation. In a preferred embodiment, targeting primers contain a 5'-phosphate group and non-targeting primers are non-phosphorylated at their 5'-ends; and a combination of Mung Bean Nuclease and λ exonuclease is used for digestion. These conditions will result in the destruction of single-stranded material by Mung Bean Nuclease, and the exonucleolytic degradation (by λ exonuclease) of any strand terminated with a 5'-phosphate group. Thus, duplexes containing both strands from the control fragment population will be degraded. Duplexes containing one 5'-phosphorylated strand (from the control fragment population) and one strand that is non-phosphorylated at the 5'-end (from the sample fragment population) will undergo degradation of the 5'-phosphorylated strand by λ exonuclease, after which the remaining strand becomes susceptible to Mung Bean Nuclease action. Duplexes consisting of two strands from the amplified sample fragment population will contain two 5'-hydroxyl termini and are thus preferentially resistant to degradation. Such duplexes are also preferentially amplifiable, as will be described below. Digestions with these enzymes may proceed in either order; in a preferred embodiment, an initial digestion with λ exonuclease is followed by treatment with Mung Bean Nuclease. Enzymes or chemical treatments which have the same specificity as Mung Bean Nuclease and λ exonuclease are also contemplated by the present invention.

G. Amplification

Following nuclease treatment, the surviving undigested polynucleotides are amplified using a non-targeting primer complementary to one of the internal primer binding sites, preferably the first internal primer binding site adjacent to the outermost primer binding site. As described supra, duplexes containing sequences unique to the sample population will have survived nuclease degradation by virtue of their non-phosphorylated 5'-ends. They will thus be available for exponential amplification. All other species of duplex or single stranded polynucleotide will have been degraded by the preceding nuclease treatment. Consequently, the amplification product will be highly enriched for fragments that are unique to the sample population.

H. Repetition of cycle to obtain further difference products

The amplified material obtained from the preceding step may be combined with an excess (2-fold to 100,000-fold, preferably 100-fold) of amplified fragments from the control population, and the cycle of annealing, nuclease digestion and amplification may be repeated until one or more desired difference products are obtained. At each cycle, a different non-targeting primer is used for the amplification step. In a preferred embodiment, the amplification primer at any given cycle will correspond to the next primer binding site internal to that used in the previous cycle. A non-targeting primer complementary to the innermost primer binding site may be used, if necessary.

The ratio of control:sample fragments is maintained at 100:1. As the rounds of subtraction proceed, rare difference products will increase in proportion in the amplified sample fragment population. This increase will allow the rare difference products to find identical matches during hybridization (a second-order kinetic reaction) more quickly. This should reduce the number of rounds of subtractive hybridization needed to find rare messages and in the later rounds may allow the long hybridization time (20 hours) to be shortened to as little as 6–8 hours, and/or permit a decrease in the number of cycles required to amplify the difference products.

To avoid obtaining "known" unwanted sequences in the difference product, the amplified control fragment population can be supplemented with the "known" sequences, or the amplified sample fragment population can be hybridized with a depletion library containing unwanted "known" sequences. Either of these methods will work most efficiently in the generation of the second (or subsequent) difference products.

Enrichment of rare messages can be enhanced by using a depleted control fragment population in the generation of the second (or subsequent) difference product. The depleted control fragment population is generated by using the control fragment population in limiting quantity and subtracting it with an excess of the sample fragment population. Depleted control fragment populations should be used in the final rounds of subtractive hybridization.

The difference products obtained by the practice of the invention may be used directly as probes, or may be cloned and propagated for sequence determination, for use as probes, etc.

EXAMPLES

In a non-limiting example of the practice of the invention, the following protocol for difference analysis between two cDNA populations is provided. TE (or 1 X TE) is 10 mM Tris-Cl (pH 8.0 at 20° C.)/0.1 mM ethylenediaminetetraacetic acid. 3X EE buffer is 30 mM EPPS (Sigma Chemical Co.), pH 8.0 (at 20° C.)/3 mM ethylenediaminetetraacetic acid.

Beveled gel loading tips are used to remove supernatant from pellets, to reduce lose of pellet due to tip displacement. To increase yield of precipitations, Hi-Yield™ tubes (Robbins Scientific Corporation, Sunnyvale, Calif.) are used. Thin walled PCR tubes (MicroAmp™ Reaction tubes, Perkin Elmer, Norwalk, Conn.) are used for the amplification steps.

Differences in cycling conditions between thermocyclers and inconsistencies between wells may be avoided by using a touchdown PCR program for the amplification steps. Don, R. H., et al., (1991) 'Touchdown' PCR to circumvent spurious priming during gene amplification. *Nucleic Acids Research* 19:4008, the disclosure of which is hereby incorporated by reference.

A. Oligonucleotides

The following oligonucleotides are prepared by automated chemical synthesis, using an Applied Biosystems 380D DNA synthesizer:

| | |
|---|---|
| AO: 45-mer adapter oligonucleotide: | |
| 5'-CGATAGTCAC TCTACCACTC AGCCTACGCA CGAGACGATG TACTC-3' | SEQ ID NO:1 |
| LA: 13-mer linker-adapter: | |
| 5'-GATCGAGTAC ATC-3' | SEQ ID NO:2 |
| P1: 22-mer oligonucleotide primer ($T_m$ = 58.4° C.) | |
| 5'-CGATAGTCAC TCTACCACTC AG-3' | SEQ ID NO:3 |
| P2: 24-mer oligonucleotide primer ($T_m$ = 61.9° C.) | |
| 5'-TAGTCACTCT ACCACTCAGC CTAC-3' | SEQ ID NO:4 |
| P3: 24-mer oligonucleotide primer ($T_m$ = 72.1° C.) | |
| 5'-TACCACTCAG CCTACGCACG AGAC-3' | SEQ ID NO:5 |
| P4: 26-mer oligonucleotide primer ($T_m$ = 74.9° C.) | |
| 5'-CAGCCTACGC ACGAGACGAT GTACTC-3' | SEQ ID NO:6 |
| PP4: 26-mer 5'-phosphate oligonucleotide primer | |
| 5'-p-CAGCCTACGC ACGAGACGAT GTACTC-3' | SEQ ID NO:7 |

B. Preparation of cDNA

PolyA⁺ mRNA is prepared from eucaryotic cells or tissues, preferably using partial lysis to generate cytoplasmic mRNA. If procaryotic cells are the source of RNA, total RNA preparations may be used. Care is taken to retain large full length transcripts (e.g., using sterile, ribonuclease-free reagents and pipettors), and to insure that samples have been treated identically, and are at similar stages of growth.

Double stranded cDNA is prepared using an oligo 5'-$T_{30}$MN-3' primer (M=A, G or C and N=A, G, C, or T), following the double-stranded cDNA production protocol that accompanies the Gibco BRL (Gaithersburg, Md.) Superscript™ II RT enzyme. Preparations of cDNA are made from both the sample and control RNA populations, under identical conditions in separate reaction vessels.

C. Restriction Digestion of cDNA

The following steps are performed identically, but in separate reaction vessels, for the sample and control cDNA populations. Two micrograms of cDNA is digested with DpnII (New England Biolabs, Inc., Beverly, Mass.), in 100 µl at 37° C. for 2 to 4 hours, under conditions recommended by the supplier, using sterile buffers and pipetting apparatus. Progress of digestion can be monitored by agarose gel electrophoresis of an aliquot of the digestion reaction. Upon completion of digestion, the digestion mixture is extracted twice with phenol/chloroform/isoamyl alcohol and once with chloroform/isoamyl alcohol. To the aqueous phase is added 2 µg glycogen carrier, 50 µl 10 M NH$_4$OAc, and 650 µl 100% EtOH. The mixture is placed on ice for 20 minutes, after which it is subjected to centrifugation at 14,000 rpm for 14 minutes at 4° C. The pellet is washed with 85% EtOH, then dried and resuspended in 20 µl TE.

D. Ligation of Adapters

The following steps are performed identically, but in separate reaction vessels, for the sample and control cDNA populations. The following components (using sterile buffers and H$_2$O) are combined:

12 µl (approx. 1.2 µg) restriction-digested cDNA (either sample fragment population or control fragment population)

7.5 µl desalted 45-mer oligo AO (2 mg/ml) [SEQ ID NO:1]

4.3 µl desalted Linker Adapter 13-mer oligo LA(1 mg/ml) [SEQ ID NO:2]

6 µl 10X Ligase Buffer (New England Biolabs, Inc., Beverly, Mass.), 27.2 µl H$_2$O To allow annealing, the mixtures are incubated in a PTC 100™ thermocycler (M J Research, Watertown, Mass.) with Hot Bonnet at 50° C. for 1 minute, followed by cooling to 10° C. over the course of 1 hour. For ligation, 3 µl T4 DNA Ligase (400 Units/µl, New England Biolabs, Beverly, Mass.) is added and incubation is continued at 12°–16° C. overnight. The ligation mixture is diluted by the addition of 140 µl TE.

E. Initial Amplification

The initial amplification reactions may be used to generate lower-complexity subsets of the sample and/or control fragment populations. This may be accomplished by choosing an appropriate combination of restriction enzyme for the restriction digestion (step C, above) and amplification conditions such that the larger fragments in the population fail to be amplified. Alternatively, the amplified population may retain the complexity of the starting material, with the initial amplification being used simply to increase the amount of material available for subsequent steps. The following conditions are designed to provide 0.5–1 mg of amplified material for each population that is amplified.

1. Sample fragment population (non-targeted)

Reactions of 200 µl are assembled in 0.5 ml microcentrifuge tubes, and 20–30 reactions are prepared. For the sample fragment population, each reaction contains the following components, added in the order shown:

169.2 µl sterile H$_2$O

20 µl 10X Vent® PCR buffer (New England Biolabs, Beverly, Mass.)

6.8 µl PCR nucleotide mix (10 mM each dATP, dCTP, dGTP, dTTP; Boehringer Mannheim, Indianapolis, Ind.)

2 µl Primer P1 (1 mg/ml) [SEQ ID NO:3]

2 µl Adapter-ligated sample fragment population, diluted as in D above

The reactions are placed in a PTC 100™ thermocycler (M J Research, Watertown, Mass.) with Hot Bonnet and incubated for 3 minutes at 72° C. (to dissociate the Linker Adapter 13-mers from step D). One microliter (5 Units) Vent® DNA polymerase (New England Biolabs, Inc., Beverly, Mass.) is added and incubation at 72° C. is continued for 5 minutes. This fills in the ends complementary to the 45-mer adapter oligonucleotide that was ligated to the fragments in step D, thereby generating a set of primer binding sites. Next, the reaction mixtures are subjected to twenty cycles of 1 minute at 95° C., 30 seconds at 58.4° C., and 3 minutes at 72° C. A final extension of 10 minutes at 72° C. is performed, then the reactions are cooled to 4° C. It is important not to increase the cycle number beyond 20, as a skewing toward smaller amplification products will occur, which will bias the subsequent subtraction. If more product is required, the number of reactions should be increased.

For purification of amplification product, four reactions are combined per 1.5 ml Eppendorf tube. Each mixture is extracted twice with 700 µl phenol/chloroform/ /isoamyl alcohol and once with chloroform/isoamyl alcohol. Then 75 µl of 3 M NaOAc (pH 5.3), and 800 µl isopropanol are added and mixed, and the tubes are placed on ice for 20 minutes. The tubes are then centrifuged at 14,000 rpm for 14 minutes at 4° C. The pellet is washed with 85% EtOH, dried, and resuspended to a nucleic acid concentration of 0.5 mg/ml (approximately 100–150 µl per four-reaction tube).

2. Control fragment population (targeted)

For the control fragment population, reactions of 200 µl are assembled in 0.5 ml microcentrifuge tubes, and 20–30 reactions are prepared. Each reaction contains the following components, added in the order shown:

169.2 µl sterile H$_2$O

20 µl 10X Vent® PCR buffer (New England Biolabs, Beverly. Mass.)

6.8 µl PCR nucleotide mix (10 mM each DATP, dCTP, dGTP, dTTP; Boehringer Mannheim, Indianapolis, Ind.)

2 µl primer PP4 (1 mg/ml) [SEQ ID NO:7]

2 µl Adapter-ligated control fragment population, diluted as in D above

The reactions are placed in a PTC 100™ thermocycler (M J Research, Watertown, Mass.) with Hot Bonnet and incubated for 3 minutes at 80° C. (to dissociate the Linker Adapter 13-mers from step D). One microliter (5 Units) Vent® (exo) DNA polymerase (New England Biolabs, Beverly, Mass.) is added and incubation at 80° C. is continued for 5 minutes. This fills in the ends complementary to the 45-mer adapter oligonucleotide that was ligated to the fragments in step D, thereby generating a set of primer binding sites. Next, the reaction mixtures are subjected to twenty cycles of 1 minute at 95° C. and 3 minutes at 74.9° C. A final extension of 10 minutes at 75° C. is performed, then the reactions are cooled to 4° C. It is important not to increase the cycle number beyond 20, as a skewing toward smaller amplification products will occur, which will bias the subsequent subtraction. If more product is required, the number of reactions should be increased.

For purification of amplification product, four reactions are combined per 1.5 ml Eppendorf tube. Each mixture is extracted twice with 700 µl phenol/chloroform/ /isoamyl alcohol and once with chloroform/isoamyl alcohol. Then 75 µl of 3 M NaOAc (pH 5.3), and 800 µl isopropanol are added and mixed, and the tubes are placed on ice for 20 minutes. The tubes are then centrifuged at 14,000 rpm for 14 minutes at 4° C. The pellet is washed with 85% EtOH, dried, and resuspended to a nucleic acid concentration of 0.5 mg/ml (approximately 100–150 µl per four-reaction tube).

F. Subtractive Hybridization

To prepare an annealing mixture, 80 µl of the amplified, adapter-ligated control fragment population from step E above (40 µg), is mixed with 40 µl of a 50-fold dilution of the amplified, adapter-ligated sample fragment population from step E above (0.4 µg), in a 0.5 ml Eppendorf microfuge tube. The mixture is extracted once with phenol/chloroform and once with chloroform. Nucleic acids are precipitated by addition of 30 µl of 10 M NH$_4$OAc, 380 µl 100% EtOH and incubation at −70° C. for 10 minutes. The mixture is warmed to 37° C. for 1 to 2 minutes (to minimize salt precipitation) and then subjected to centrifugation at 14,000 rpm for 14 minutes at 4° C. The pellet is washed twice with 85% EtOH, with brief centrifugation each time, then dried by vacuum for three minutes.

The pellet is resuspended thoroughly in 4 µl 3X EE buffer [30 mM EPPS (Sigma Chemical Co.), pH 8.0 (at 20° C.)/3 mM EDTA] by pipetting for at least 2 minutes, then warmed to 37° C. for 5 minutes. The contents are mixed by vortexing and the liquid is brought to the bottom of the tube by a brief centrifugation, then overlain with 35 µl of mineral oil, prewarmed to 37° C.

The mixture is then incubated at 98° C. for 5 minutes in a thermocycler to denature the nucleic acids. It is cooled to 67° C., and 1 µl of 5 M NaCl (pre-warmed to 67° C.) is immediately added directly into the subtractive hybridization mixture. Incubation at 67° C. is continued for 20 hours.

G. Generation of First Difference Product (DP1)

1. Dilution of subtractive hybridization mixture

The subtractive hybridization mixture is removed from under the mineral oil and diluted stepwise, using preheated solutions to minimize unwanted hybridization induced by changes in temperature. First, the subtractive hybridization mixture from step F above, having been incubated for 20 hours at 67° C., is added to 15 µl TE, that has been prewarmed to 67° C. Keeping the tube in the thermocycler, the mixture is pipetted vigorously. An additional 65 µl TE (prewarmed to 67° C.) is added, and the mixture is once again pipetted vigorously. Finally, 315 µl sterile H$_2$O (prewarmed to 67° C.) is added, and the mixture is vortexed thoroughly. Subtractive hybridization mix is now at 0.2X TE and ready for either λ exonuclease digestion or Mung Bean Nuclease digestion. It can be stored on ice or frozen at −70° C. for long-term storage.

2. Digestion with λ Exonuclease

To 200 µl of the diluted subtractive hybridization mixture from step G.1 above is added 30 µl 10 X λ Exonuclease Buffer (Pharmacia Biotech, Piscataway, N.J.), 60 µl water and 10 µl λ Exonuclease (10 Units/µl, Pharmacia Biotech, Piscataway, N.J.). The reaction mixture is incubated at 37° C. for 30 minutes. Digestion is terminated by incubation of the reaction mixture at 75° C. for 10 minutes, followed by cooling to room temperature for 5 minutes. the reaction tube is centrifuged briefly to collect the condensate and 100 µl of water is added and mixed. The reaction mixture is extracted twice with an equal volume of phenol/chloroform/isoamyl alcohol (25:24:1, v/v/v) and once with an equal volume of chloroform/isoamyl alcohol (24:1, v/v). The aqueous phase is divided (200 µl into each of two 1.5 ml microfuge tubes), and to each tube is added 4 µg glycogen carrier, 0.1 ml of 10 M ammonium acetate, and 1.3 ml of absolute ethanol. After mixing and incubation on dry ice for 20 min, precipitated nucleic acid is collected by centrifugation at 14,000 rpm for 14 min at 4° C. The pellets are washed with 85% ethanol, vacuum dessicated for 3 min and resuspended in 50 µl of sterile water per pellet. The resuspended pellets are combined into one of the two tubes, the other is washed twice with 50 µl of sterile water and the washes are combined with the resuspended pellets.

As a positive control for the exonuclease digestions, a set of commercially available, 5'-phosphorylated molecular weight markers can be used. As a negative control, the same markers can be dephosphorylated (for example, by treatment with bacterial or calf intestine alkaline phosphatases). The presence or absence of digestion products can be detected by Southern blotting analysis.

3. Mung Bean Nuclease Digestion

To 200 µl of the λ exonuclease digestion mixture from step G.2 above, the following components are added:

40 µl 10 X Mung Bean Nuclease Buffer (New Eng. Biolabs, Beverly, Mass.)

4 µl ZnSO$_4$

136 µsterile H$_2$O

20 µl Mung Bean Nuclease (10 Units/µl, New Eng. Biolabs, Beverly, Mass.)

The digestion mixture is incubated at 30° C. for 35 minutes. It is then extracted twice with phenol/chlorofonn/ isoamyl alcohol and once with chloroform/isoamyl alcohol, and divided into two 1.5 ml microfuge tubes containing 200 µl each. After addition of 4 µg of glycogen carrier, 100 µl of 10 M NH$_4$OAc, and 1300 µl of 100% EtOH, the mixture is placed on dry ice for 20 minutes. Nucleic acids are collected by centrifugation at 14,000 rpm for 14 minutes at 4° C. The pellets are washed with 85% EtOH, vacuum desiccated for 3 minutes and each is resuspended in 50 µl sterile water. Nucleic acids may be purified from the Mung Bean Nuclease reaction using the Pharmacia Microspin™ Column S-200 (Pharmacia Biotech, Piscataway, N.J.) following the protocol provided by the manufacturer. Column effluents are combined.

4. Amplification

Twenty microliters of the Mung Bean Nuclease/λ Exonuclease-digested material from step G.3 is added, on ice, to each of four tubes, each of which contains the following components, which have been preassembled on ice:

169.2 µl sterile H$_2$O

20 µl 10X Vent® buffer (New England Biolabs, Beverly, Mass.)

6.8 µl PCR nucleotide mix (10 mM each DATP, dCTP, dGTP, dTTP; Boehringer Mannheim, Indianapolis, Ind.)

2 µl P2 primer (1 mg/ml) [SEQ ID NO:4]

The mixtures are incubated in a thermocycler for 1 minute at 95° C., then cooled to 80° C., whereupon 1 µl (5 Units) of Vent® (exo) DNA polymerase (New England Biolabs, Beverly, Mass.) is added. Twenty-two amplification cycles are then carried out according to the following protocol: 1 minute at 95° C., 30 seconds at 61.9° C. and 3 minutes at 72° C. A final extension of 5 minutes at 72° C. is conducted, and the reactions are cooled to 4° C.

The 4 amplification reactions are then combined into one 1.5 ml Eppendorf tube, extracted twice with phenol/ chloroform/isoamyl alcohol and once with chloroform/ isoamyl alcohol. Nucleic acids are precipitated by the addition of 75 µl of 3 M NaOAc (pH 5.3) and 800 µl of isopropanol, followed by incubation on ice for 20 minutes. The precipitate is collected by centrifugation at 14,000 rpm for 14 minutes at 4° C. Pellets are washed with 85% EtOH, vacuum desiccated for 3 minutes and resuspended in 100 µl of TE, to give a nucleic acid concentration of approximately 0.5 µg/µl. This is Difference Product 1 (DP1).

H. Generation of Second Difference Product (DP2)

DP-1 is diluted to 10 ng/µl with TE. The steps of subtractive hybridization (F), dilution (G. 1), Mung Bean Nuclease Digestion (G.2), λ Exonuclease digestion (G.3), and amplification (G.4) are repeated, following the procedures described above, with the following changes. In step F, DP-1 is substituted for the amplified, adapter-ligated sample fragment population; in step G.4, the P3 primer [SEQ ID NO: 5] is substituted for the P2 primer [SEQ ID NO: 4] and the following cycling program is used for amplification using the P3 primer: 1 minute at 95° C. and 3 minutes at 72.1° C.

I. Generation of Third Difference Product (DP3)

DP-2 is diluted to 10 ng/μl with TE. The steps of subtractive hybridization (F), dilution (G. 1), Mung Bean Nuclease Digestion (G.2), λ Exonuclease digestion (G.3), and amplification (G.4) are repeated, following the procedures described above, with the following changes. In step F, DP-2 is substituted for the amplified, adapter-ligated sample fragment population; in step G.4, the P4 primer [SEQ ID NO: 6] is substituted for the P2 primer [SEQ ID NO:4] and the following cycling program is used for amplification using the P4 primer: 1 minute at 95° C. and 3 minutes at 74.9° C.

J. Analysis of Difference Products

If desired, any of the difference products may be analyzed by restriction digestion and gel electrophoresis, as follows. The DNA concentration of the difference product is determined (for example, by ultraviolet absorbance) and DNA is digested according to the following protocol. Combine:

1.0 μl (500 ng) DNA (DP1, DP2 or DP3)
1.0 μl 10X Dpn II Buffer (New England Biolabs, Beverly, Mass.)
0.5 μl Dpn II (50 U/μl, New England Biolabs, Beverly, Mass.)
7.5 μl sterile $H_2O$ The digestion mixture is incubated at 37° C. for 2 to 4 hours. Digestion products (500 ng), along with 500 ng aliquots of undigested difference product; amplified, adapter-ligated control fragment population; and amplified, adapter-ligated sample fragment population are analyzed on a 2.0% Seakem® GTG® (FMC BioProducts, Rockland, Me.) agarose mini-gel run in TAE buffer (40 mM Tris-acetate/10 mM ethylene-diaminetetraacetic acid, pH 8.3 at 23° C.). Marker lanes include 1 μg each of markers IX and III (Boehringer Mannheim, Indianapolis, Ind.).

The amplification products should range in size from 200–1300 base pairs. As the number of rounds of subtractive hybridization/selective amplification increases the presence of individual discrete bands should increase in intensity. If the bands are smeary reamplify with diluted sample fragments and/or decrease the number of amplification cycles. Finally, it is always preferable to use PCR in a Hotstart format.

While the present invention has been described above by certain specific examples and embodiments, it is limited only by the scope of the appended claims.

What is claimed is:

1. A method for producing a difference product between an initial sample population of polynucleotides and an initial control population of polynucleotides, the method comprising:

(a) covalently attaching, to the polynucleotides in both populations, an oligonucleotide comprising multiple primer binding sites, said multiple primer binding sites comprising an outermost primer binding site, an innermost primer binding site, and one or more internal primer binding sites therebetween, to produce marked sample and control polynucleotide populations;

(b) amplifying the marked sample polynucleotide population using a non-targeting primer complementary to the outermost primer binding site of said oligonucleotide to generate an amplified sample polynucleotide population;

(c) amplifying the marked control polynucleotide population using a targeting primer complementary to the innermost primer binding site of said oligonucleotide to generate an amplified control polynucleotide population;

(d) combining said amplified sample polynucleotide population with an excess of said amplified control polynucleotide population, denaturing, and incubating under annealing conditions to produce an annealing mixture;

(e) subjecting the annealing mixture to conditions under which all polynucleotides in said mixture will be degraded, except for double-stranded polynucleotides containing a non-targeting primer in each strand, to generate a treated annealing mixture; and (f) subsequently subjecting the treated annealing mixture to amplification, using a non-targeting primer complementary to one of said internal primer binding sites, to produce said difference product.

2. The method according to claim 1 further comprising reiterative repetition of a cycle of steps comprising steps (d) through (f), wherein, at the first iteration, the difference product produced by step (f) is substituted for the amplified sample polynucleotide population in step (d) and, at subsequent iterations, the difference product produced by the previous cycle is substituted for the amplified sample polynucleotide population in step (d), and further wherein, at each iteration, the treated annealing mixture in step (f) is subjected to said amplification using a non-targeting primer complementary to a primer binding site different from that used in the preceding cycle, to produce an additional difference product.

3. The method according to claim 1 wherein said both populations in step (a) are lower-complexity subsets of the initial sample and control polynucleotide populations.

4. The method according to claim 3 wherein, in steps (b) and (c), the amplification is conducted under conditions wherein the degree of amplification is limited, thereby generating said amplified sample and control polynucleotide populations, which are lower-complexity subsets of the marked sample and control polynucleotide populations.

5. The method according to claim 1 wherein the initial sample and control polynucleotide populations are subjected to fragmentation prior to the covalent attachment.

6. The method according to claim 5, wherein said fragmentation is achieved by restriction endonuclease digestion.

7. The method according to claim 1, wherein the targeting primer contains a 5'-phosphate group and the non-targeting primer lacks a 5'-phosphate group.

8. The method according to claim 6, wherein, in step (e), said conditions comprise the activities of a single strand-specific nuclease and an exonuclease specific for 5'-phosphate-terminated nucleic acids.

9. The method according to claim 8, wherein the single-strand-specific nuclease is Mung Bean Nuclease.

10. The method according to claim 8, wherein the exonuclease specific for 5'-phosphate-terminated nucleic acids is λ exonuclease.

11. The method according to claim 1, wherein the covalent attachment is by enzymatic ligation.

12. The method according to claim 1, wherein said primer binding sites have different annealing temperatures.

13. The method according to claim 12, wherein each primer binding site, progressing from outermost to innermost, has a successively higher annealing temperature.

14. The method according to claim 13, wherein said oligonucleotide contains four primer binding sites.

15. The method according to claim 2, wherein said amplification is performed by a polymerase chain reaction.

16. The method according to claim 15, wherein less than 22 cycles of a polymerase chain reaction are used to generate each difference product.

17. The method according to claim 3 wherein said initial sample and control polynucleotide populations comprise genomic DNA.

18. The method according to claim 1 wherein said initial sample and control polynucleotide populations comprise cDNA.

19. The method according to claim 1 wherein the annealing mixture contains magnesium to facilitate annealing.

20. The method according to claim 2 further comprising cloning at least one of the difference products.

21. The method according to claim 1 wherein one or more of the multiple primer binding sites overlaps one or more of the other primer binding sites.

* * * * *

UNITED STATES PATENT AND TRADEMARK OFFICE
CERTIFICATE OF CORRECTION

PATENT NO. : 5,958,738
DATED : September 28, 1999
INVENTOR(S) : Garrett LINDEMANN and Paula SCHUELER It is certified that error appears in the above-identified patent and that said Letters Patent is hereby corrected as shown below:

In claim 8, at column 31, line 24, please replace "6" with --7--.

Signed and Sealed this

Twenty-eighth Day of December, 1999

Attest:

Attesting Officer

Q. TODD DICKINSON

Acting Commissioner of Patents and Trademarks